United States Patent

Fukuda et al.

(10) Patent No.: US 7,498,579 B2
(45) Date of Patent: Mar. 3, 2009

(54) SCINTILLATOR AND RADIATION DETECTOR, AND RADIATION INSPECTING DEVICE

(75) Inventors: Tsuguo Fukuda, Sendai (JP); Hirohisa Kikuyama, Izumiootsu (JP); Tomohiko Satonaga, Izumiootsu (JP); Hikaru Koike, Yamanshi (JP)

(73) Assignee: Stella Chemifa Corporation, Osaka (JP)

( * ) Notice: Subject to any disclaimer, the term of this patent is extended or adjusted under 35 U.S.C. 154(b) by 335 days.

(21) Appl. No.: 10/569,488

(22) PCT Filed: Aug. 25, 2004

(86) PCT No.: PCT/JP2004/012189

§ 371 (c)(1),
(2), (4) Date: Jun. 23, 2006

(87) PCT Pub. No.: WO2005/019862

PCT Pub. Date: Mar. 3, 2005

(65) Prior Publication Data

US 2007/0018107 A1    Jan. 25, 2007

(30) Foreign Application Priority Data

Aug. 25, 2003    (JP)    ............... 2003-300646

(51) Int. Cl.
*G01T 1/20*    (2006.01)
*C09K 11/02*    (2006.01)

(52) U.S. Cl. ............. 250/361 R; 252/301.4 R
(58) Field of Classification Search ............. 250/361 R; 252/301.4 R
See application file for complete search history.

(56) References Cited

U.S. PATENT DOCUMENTS

2005/0015004 A1* 1/2005 Hetel et al. ............... 600/425
2006/0000977 A1* 1/2006 Juestel et al. ........... 250/361 R

FOREIGN PATENT DOCUMENTS

| JP | 4-9688 | 1/1992 |
| JP | 5-87934 | 4/1993 |
| JP | 2002-350597 | 12/2002 |
| JP | 2003-107160 | 4/2003 |

OTHER PUBLICATIONS

Tomohiko Satonaga et al., "Micro Hikisageho ni yoru AE (=Ca, Ba) $F_2$ Oyobi RE (=Pr,Ce) $F_3$ Kessho no Ikusei", Jinko Kessho Toronkai Koen Yoshishu, Nov. 4, 2003, vol. 48, pp. 35 to 36.

* cited by examiner

*Primary Examiner*—David P Porta
*Assistant Examiner*—Mindy Vu
(74) *Attorney, Agent, or Firm*—Young & Thompson

(57)    ABSTRACT

A scintillator, characterized in that it comprises crystals of $Pr_{1-x}Ce_xF_3$ [wherein 0<x<0.5]. It emits a light in ultraviolet and visible regions when it is irradiated with a light or a radiation. The scintillator uses a material which exhibits improved performance with respect to the strength in light emission and to the speed in attenuation, and further is relatively easy in the growth of its crystal.

12 Claims, 1 Drawing Sheet

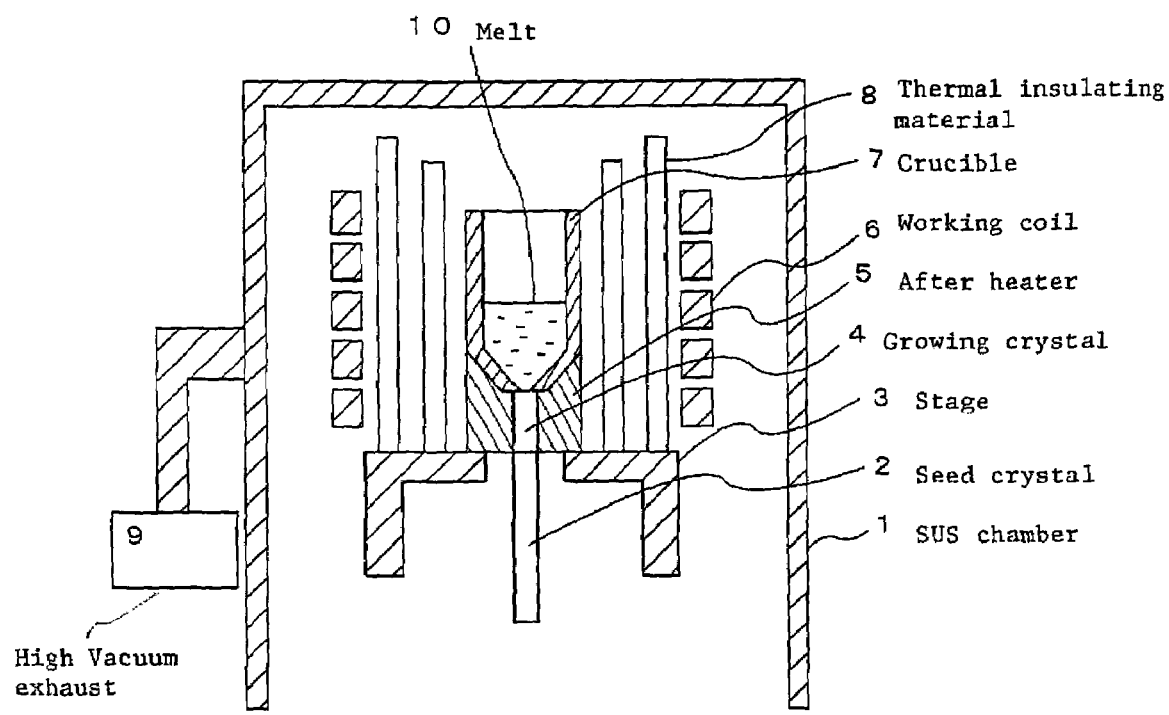

SCINTILLATOR AND RADIATION DETECTOR, AND RADIATION INSPECTING DEVICE

This is a 371 national stage application of International Application No. PCT/JP2004/012189; filed Aug. 25, 2004, which claims priority to Japanese Application No. 2003-300646, filed Aug. 25, 2003. The entire contents of the above-referenced applications are hereby incorporated by reference in their entirety.

FIELD OF THE INVENTION

This invention relates to various radiation detectors' scintillators and radiation detectors, and radiation inspecting devices.

BACKGROUND OF THE INVENTION

Patent document 1: Japanese Patent Laid-Open No. 5-87934

The scintillator crystals are used in many fields as detectors of various radiations, such as X-ray and γ-ray. Required characteristics for the scintillator crystals are somewhat changed depending on their uses, but generally involve:
  a high density;
  a large fluorescence output by applying radiation;
  a high fluorescence attenuation rate:
  good radiation tolerance:
  a crystal having no deliquescence or cleavability, and easy to be processed In these days, taking into account these requirements, crystals adopting active Ce with high
  attenuation rate (20-60 ns) are often used. For example, $Gd_2SiO_5$:Ce (GSO), $Lu_2SiO_5$:Ce (LSO) and the like are used in the medical diagnostic equipments, such as PET (positron emission tomography), but the above-mentioned required characteristics are not necessarily satisfied sufficiently and there are problems that: in GSO, the crystal raising requires high techniques due to strong crystal anisotropy and becomes the hindrance of cost reduction, and in LSO, the fluorescence output has variations between samples.

Also, as the scintillators using Pr, Ce and F, those consisting of $Gd_2O_2$:Pr, Ce and F have been known as described in Patent document 1.

However, even among the scintillators according to Patent-documents 1, scintillators with stable characteristics (especially fluorescence output) have not yet been obtained.

SUMMARY OF THE INVENTION

Problems to be Solved by the Invention

The present invention aims to provide a scintillator having high and stable fluorescence output, crystal raising thereof being comparatively easy.

The present invention aims to provide a radiation detector having high and stable detection sensitivity.

The present invention aims to provide a medical radiodiagnosis device which can obtain captured images with high-resolution.

Means for Solving the Problems

The present invention focused attention on the high density rare earth fluorides. Among them, by combining $CeF_3$, which includes $Ce^{3+}$ from which luminescence with a short attenuation time (50 ns or less) is expected, with $PrF_3$, which is of higher density than $CeF_3$ and makes solid solution with $CeF_3$ easily due to the same crystal structure (tysonite type) as $CeF_3$ and grows into crystals easily, the present invention found out a stable scintillator with higher fluorescence output and of higher density (about 6.28 g/cm$^3$) than $CeF_3$, with the attenuation time shorter than GSO (56 ns) and LSO (47 ns), without variations in fluorescence output because of the uniform Ce concentration achieved by the same crystal structures and by making solid solution. The inventors further studied wholeheartedly and found out that increase in the above-mentioned luminescence output was caused by the energy transition from the mother crystal, $PrF_3$, to $Ce^{3+}$.

Specifically speaking, the scintillator of the present invention is characterized by consisting of a crystal of $Pr_{1-x}Ce_xF_3$ (0<x<0.5).

In particular, 0.03<x<0.2 is preferred.

The radiation detector of the present invention is characterized by consisting of a combination of the above-mentioned scintillator and a light responding means.

The radiation inspecting device of the present invention is characterized by being provided with the above radiation detector as its radiation detector.

Effect of the Invention

According to the present invention, it has become possible to provide a scintillator wherein the performance is high with respect to luminescence intensity and attenuation rate, and specifically speaking, the luminescence intensity is stronger and the density is higher than $CeF_3$, the attenuation time is shorter than GSO and LSO, and moreover, crystal raising is comparatively easy.

It has become possible to provide a radiation detector whose detection sensitivity is high and fluorescence output is stable.

It has become possible to provide a radiation inspecting device which can obtain captured images with high-resolution. As the radiation inspecting device, PET (positron emission tomography) is preferred, for example. As for the PET (positron emission tomography), a two-dimensional type PET, a three-dimensional type PET, a time-of-flight (TOF) type PET, a depth-of-image (DOI) type PET, or combination thereof, are more preferred. Further, the PET apparatus is preferred to be a single device, or a combination with any of MRI, CT or SPECT, or with two of them.

BRIEF EXPLANATION OF THE DRAWINGS

FIGURE. A schematic diagram of an atmosphere control high-frequency-induction-heating type micro pulling down apparatus.

EXPLANATIONS OF LETTERS OR NUMERALS

1 SUS Chamber
2 Seed Crystal
3 Stage
4 Growing Crystal
5 After Heater
6 Working Coil
7 Crucible
8 Thermal Insulating Material
9 Exhaust
10 Melt

THE BEST MODE FOR CARRYING OUT THE INVENTION (Scintillator Composition: $Pr_{1-x}Ce_xF_3$)

The scintillator emits a light in ultraviolet or visible region, when it is irradiated with a light or a radiation.

The scintillator of the present invention consists of a crystal having composition of $Pr_{1-x}Ce_xF_3$, wherein $0<x<0.5$.

When cerium is not doped to praseodymium fluoride (in the case of x=0), if X-ray is irradiated thereon, luminescence originating from $Pr^{3+}$ is observed at 400 nm, and the attenuation time thereof is very slow, about 600 ns. However, when cerium is doped, luminescence at 400 nm originating from $Pr^{3+}$ decreases, and instead, luminescence originating from $Ce^{3+}$ appears near 290 nm. The attenuation time thereof is from 17 to 17.5 ns, which is faster than 27 ns of $CeF_3$ used for energy measurement of high energy γ-ray. As the added cerium concentration is increased, the luminescence intensity at 290 nm further increases and the luminescence at 400 nm loses its intensity.

Particularly, in the case of $0.03<x<0.2$, the luminescence intensity at 290 nm becomes large to give the luminescence intensity equivalent to or beyond that of $CeF_3$ which is comparatively strong among the fluorides.

However, when x is 0.5 or larger, the luminescence intensity at 290 nm decreases.

(Manufacturing Method of the Scintillator)

The scintillator crystal of the above-mentioned composition is preferred, but not limited, to be grown by the micro pulling down method or by the general crystal growing methods such as the Czochralski method, the Bridgman method, or the floating zone method.

Among them, the micro pulling down method allows crystal to grow at a speed one or two digit higher than usual melt growth method. Therefore, the required time to grow crystal is short, and single crystals of significant size and quality can be obtained from small amount of materials.

For example, x can be controlled by raw material. What is necessary is just to calculate the amounts of the raw materials, $PrF_3$ and $CeF_3$ so that predetermined x may be obtained. Predetermined amounts of $PrF_3$ and $CeF_3$ may be mixed and fused in a crucible.

Since the conventional scintillator was mainly manufactured by sintering, the composition control thereof has been difficult, but by manufacturing the scintillator by the above-mentioned crystal growing method, production of the crystal whose compositions are fully controlled can be attained.

(Radiation Detector)

The radiation detector of the present invention consists of a combination of the scintillator and a light responding means.

The light responding means converts luminescence from the scintillator into an electric signal. For example, photoelectric conversion elements, such as a photodiode may be used. A photomultiplier element may be also provided.

(Radiation Inspecting Device)

Providing a radiation detector as a radiation detector will make an apparatus effective in detecting the radiations in various fields.

A method for acquiring structural or compositional information of a subject as a two-dimensional image by irradiating the subject with various radiations such as X-ray, neutron beam and γ-ray, and measuring the intensity distributions of the radiation penetrated through the subject with a radiation detector (radiography), can be widely utilized, as X-ray diagnostic devices in the medical field, dangerous materials detecting devices for baggage, and nondestructive inspection devices for various constructions.

For example, PET (the positron emission tomography) is one of the tomogram method used in the nuclear medicine diagnosis, in which the radioactive drug labeled by the positron emission nuclide is administered to the subject, an annihilation radiation emitted from inside the body is externally detected, and the concentration distribution of the drug is obtained as a tomogram image. Since living body functions, such as bloodstream and metabolic activities of glucose can be examined on real time, it is effective in complicated cerebral function research and early detection of cancer and dementia.

Also, the neutron radiography is a method for acquiring structural or compositional information of the subject as two-dimensional images, by detecting the intensity distribution of the thermal neutron beam penetrated through the subject and attenuated. It is effective in examination of hydrogen containing compounds and composite materials comprising metals and the light element substances which are difficult to be examined by the X-ray or the γ-ray, and is utilized as an effective examination method in the wide fields such as plant apparatus, airplanes, auto parts and the like.

An X-ray diagnostic device (CT scanner) arranges many X-ray detectors around the patient as a subject, the signals of the penetrated X-rays received by these detectors are reconstructed as tomograms by computer-operated processing, and the tomograms are displayed on an image display apparatus such as CRT or obtained as a photograph. Since the tomograms by this X-ray diagnostic device are obtained as slice images of a human body unlike the usual X-ray photographs and the like, it becomes possible to diagnose the disease in the depths of the human body such as internal organs with high precision.

Also the radiation detector of the present invention is applicable in the environmental measurement devices and in the fields of various computer processing radiography which detect nuclear radiations.

COMPARATIVE EXAMPLE 1

Among the crystals of the present invention, $Pr_{1-x}Ce_xF_3$, that of x=0.01 was grown by the fluoride micro PD method. High purity $PrF_3$ and $CeF_3$ as the materials were weighed and mixed, and then were charged in a high purity platinum crucible with a small pore at the bottom. As shown in the FIGURE, a seed, a stage, after heater, thermal insulating material, and the crucible charged with materials were arranged, and were heated to 700° C. in vacuo exhausted to about $1\times10^{-3}$ Pa with an oil rotary pump and an oil, diffusion pump. Then, the inside of the chamber was replaced by Ar gas. The sample was then melted by being heated to about 1450° C. with a high frequency coil. The bottom of the crucible was monitored with a CCD camera. When the melt appeared from the small pore at the crucible bottom, a seed crystal was attached to it and was pulled down at a rate 0.05-0.5 mm/min to be solidified. As a result, a green clear crystal with φ3 mm and 50 mm in length was obtained. When the obtained crystal was irradiated by X-ray at room temperature, strong luminescence was observed at 290 nm, and also at 400 nm.

EXAMPLE 1

Among the crystals of the present invention, $Pr_{1-x}Ce_xF_3$, that of x=0.03 was grown by the fluoride micro PD method. The crystal was grown in the same way as Comparative Example 1, and a green clear crystal 50 mm in length was obtained. When the obtained crystal was irradiated by the X-ray at room temperature, strong luminescence was observed at 290 nm, which was stronger than in Example 1. Luminescence was also observed at 400 nm, but it was smaller than in Example 1. In this way, the effect of increase in the concentration of added cerium was observed. When an attenuation time of the luminescence at 290 nm was measured by ultraviolet light excitation, it was 17-17.5 ns. It was 20.5 ns, when the attenuation time by X-ray excitation was measured.

EXAMPLE 2

In this example, x was further changed among 0, 0.001, 0.01, 0.03, 0.06, 0.1, and 0.2. Crystal was grown in the same way as Comparative Example 1, and a green clear crystals of 20-50 mm in length were obtained.

The above luminescence data were shown in Table 1.

TABLE 1

| X (in $Pr_{1-x}Ce_xF_3$) | Luminescence intensity at 290 nm (originated from $Ce^{3+}$) *1 | Luminescence intensity at 400 nm (originated from $Pr^{3+}$) *2 |
|---|---|---|
| 0 | 0 | 100 |
| 0.001 | 10 | 90 |
| 0.01 | 50 | 30 |
| 0.03 | 70 | 15 |
| 0.06 | 100 | 0 |
| 0.1 | 120 | 0 |
| 0.2 | 100 | 0 |
| 0.5 | 20 | 0 |
| 0.6 | 5 | 0 |

*1 Setting $CeF_3$ as 100
*2 Setting $PrF_3$ as 100.

EXAMPLE 3

In this example, the crystal of x=0.1 in $Pr_{1-x}Ce_xF_3$, was grown by the Czochralski method. Materials, high purity $PrF_3$ and $CeF_3$, were weighed and mixed, and then were charged in a carbon crucible. This was installed in a growing furnace, heated to 700° C. in vacuo exhausted to about $1 \times 10^{-3}$ Pa with an oil rotary pump and an oil diffusion pump. Then, the inside of the chamber was substituted by Ar gas, heated to about 1450° C. with a high frequency coil to melt the sample. When the temperature became stable, the sample was contacted with the seed crystal, and the crystal was grown at the pull-up speed of 1 mm/h, rotating at 10-20 rpm. A green clear crystal without crack with 50 mm in diameter and about 150 mm in length was obtained. When the obtained crystal was irradiated by the X-ray at room temperature, strong luminescence was observed at 290 nm, and a similar result to Example 2 was obtained.

Thus, $Pr_{1-x}Ce_xF_3$ (0<x<0.5) of the present invention had higher density than $CeF_3$ (6.16 g/cm$^3$), and the luminescence intensity thereof was shown to be equal or more than comparable to $CeF_3$. The lifetime of fluorescence was also shorter than GSO (56 ns) and LSO (47 ns) in which Ce was used. It obviously showed outstanding scintillator characteristics.

INDUSTRIAL APPLICABILITY

According to the present invention, it has become possible to provide a scintillator having high performances with respect to luminescence intensity and attenuation rate, and specifically speaking, having stronger luminescence intensity and higher density than $CeF_3$ and attenuation time shorter than GSO and LSO, and moreover, the crystal growing thereof being comparatively easy.

It has become possible to provide a radiation detector having high detection sensitivity and stable fluorescence output.

It has become also possible to provide a radiation inspecting device capable of obtaining captured images with high-resolution. As the radiation inspecting device, PET (positron emission tomography) is preferred, for example. As for the PET (positron emission tomography), two-dimensional type PET, three-dimensional type PET, time-of-flight (TOF) type PET, depth-of-image (DOI) type PET, or combination thereof, are more preferred. Further, as for a PET apparatus, it is preferred that it is a single device, or a combination with any of MRI, CT, or SPECT, or two of them.

The invention claimed is:

1. A scintillator consisting of a crystal of $Pr_{1-x}Ce_xF_3$ in which 0<x<0.5.

2. The scintillator according to claim 1, wherein 0.03<x<0.2.

3. The scintillator according to claim 2, wherein said crystal is grown by a micro pulling down method, a Czochralski method, a floating zone method, or a Bridgman method.

4. A radiation detector consisting of a combination of the scintillator according to claim 2 and a light responding means.

5. The scintillator according to claim 1, wherein said crystal is grown by a micro pulling down method, a Czochralski method, a floating zone method, or a Bridgman method.

6. A radiation detector consisting of a combination of the scintillator according to claim 5 and a light responding means.

7. A radiation detector consisting of a combination of the scintillator according to claim 1 and a light responding means.

8. A radiation inspecting device comprising a radiation detector consisting of a combination of the scintillator of claim 1 and a light responding means.

9. The radiation inspecting device according to claim 8, wherein said radiation inspecting device is an X-ray CT scanner.

10. The radiation inspecting device according to claim 8, wherein said radiation inspecting device is PET (positron emission tomography).

11. The radiation inspecting device according to claim 10, wherein said PET is two-dimensional type PET, three-dimensional type PET, time-of-flight (TOF) type PET, depth-of-image (DOI) type PET, or a combination type thereof.

12. The radiation inspecting device according to claim 8, wherein said radiation inspecting device is a single device, or a combination type with one or two of MRI, CT or SPECT.

* * * * *